(12) United States Patent
Nord

(10) Patent No.: US 8,411,819 B2
(45) Date of Patent: Apr. 2, 2013

(54) RADIATION TREATMENT PLANNING AND EXECUTION THAT CONSIDER THE TYPE OF CRITICAL ORGAN

(75) Inventor: Janne Nord, Espoo (FI)

(73) Assignee: Varian Medical Systems International AG, Zug (CH)

( * ) Notice: Subject to any disclaimer, the term of this patent is extended or adjusted under 35 U.S.C. 154(b) by 376 days.

(21) Appl. No.: 12/354,465

(22) Filed: Jan. 15, 2009

(65) Prior Publication Data

US 2010/0177871 A1  Jul. 15, 2010

(51) Int. Cl.
*A61N 5/10* (2006.01)
(52) U.S. Cl. .......................................... 378/65; 378/64
(58) Field of Classification Search .................. 378/65, 378/64
See application file for complete search history.

(56) References Cited

U.S. PATENT DOCUMENTS

| 6,888,919 | B2 | 5/2005 | Graf | |
| 7,649,981 | B2 | 1/2010 | Seppi et al. | |
| 2004/0008822 | A1* | 1/2004 | Bortfeld et al. | 378/210 |
| 2008/0021300 | A1* | 1/2008 | Allison | 600/407 |

* cited by examiner

*Primary Examiner* — Hoon Song
(74) *Attorney, Agent, or Firm* — Vista IP Law Group, LLP

(57) ABSTRACT

A method for use in a treatment planning process or in a treatment process includes determining a type of critical organ for healthy tissue, and accumulating dose for the healthy tissue based on the type of critical organ.

A method for use in a treatment planning process or in a treatment process includes determining a type of critical organ for healthy tissue, and determining a constraint for the healthy tissue, wherein the constraint is determined based on different movement trajectories and the type of critical organ.

48 Claims, 6 Drawing Sheets

RADIATION TREATMENT PLANNING AND EXECUTION THAT CONSIDER THE TYPE OF CRITICAL ORGAN

FIELD

This application relates generally to radiation therapy, and more specifically, to radiation treatment planning and execution.

BACKGROUND

Radiation therapy has been employed to treat tumorous tissue. In radiation therapy, a high energy beam is applied from an external source towards the patient. The external source, which may be rotating (as in the case for arc therapy), produces a collimated beam of radiation that is directed into the patient to the target site. The dose and placement of the dose must be accurately controlled to ensure that the tumor receives sufficient radiation, and that damage to the surrounding healthy tissue is minimized.

Sometimes, in a radiation treatment procedure, a plurality of treatment sessions may be performed. In each treatment session, a radiation source may be placed at a prescribed gantry angle to thereby deliver radiation beam towards a target tissue from a certain angle. As a result of delivering radiation towards the target tissue from a plurality of different angles, a sufficient radiation dose may be delivered to the target tissue to thereby treat the target tissue, while surrounding healthy tissue may be protected.

It has been known that delivering radiation towards a target tissue from different angles may result in creation of hotspot(s) at critical organ(s) that contains healthy tissue. Currently, hotspots are attempted to be minimized or reduced by drawing or inputting artificial structures representing normal (healthy) tissues into a computer program. Thereafter, the computer program imposes a constraint (representing a limit on radiation dose to be received by the critical organ) on the drawn artificial structures, and determines a treatment plan based on the imposed constraint. In existing techniques, different critical organs with different biological characteristics are considered the same way during treatment planning and treatment execution. For examples, radiation doses (simulated or actual) delivered to different critical organs are accumulated using the same technique. Also, in existing techniques, the same type of dose constraint may be imposed for different critical organs. Inventor of the subject case determines that such existing techniques may not provide a desired treatment plan or a desired treatment result since different critical organs have different biological characteristics, and therefore, should be considered differently during treatment planning and execution.

SUMMARY

In accordance with some embodiments, a method for use in a treatment planning process or in a treatment process includes determining a type of critical organ for healthy tissue, and accumulating dose for the healthy tissue based on the type of critical organ.

In accordance with other embodiments, a system for use in a treatment planning process or in a treatment process, includes a processor configured for determining a type of critical organ for healthy tissue, and accumulating dose for the healthy tissue based on the type of critical organ.

In accordance with other embodiments, a method for use in a treatment planning process or in a treatment process includes determining a type of critical organ for healthy tissue, and determining a type of constraint for the healthy tissue based on the determined type of critical organ.

In accordance with other embodiments, a system for use in a treatment planning process or in a treatment process includes a processor configured for receiving information regarding a type of critical organ for healthy tissue, wherein the processor is also configured for providing a type of constraint for the healthy tissue based on the type of critical organ.

In accordance with other embodiments, a method for use in a treatment planning process or in a treatment process includes determining a type of critical organ for healthy tissue, and determining a constraint for the healthy tissue, wherein the constraint is determined based on different movement trajectories and the type of critical organ.

In accordance with other embodiments, a system for use in a treatment planning process or in a treatment process includes a processor configured for receiving information regarding a type of critical organ for healthy tissue, wherein the processor is also configured for determining a constraint for the healthy tissue by based on different movement trajectories and the type of critical organ.

Other and further aspects and features will be evident from reading the following detailed description of the embodiments, which are intended to illustrate, not limit, the invention.

BRIEF DESCRIPTION OF THE DRAWINGS

The drawings illustrate the design and utility of embodiments, in which similar elements are referred to by common reference numerals. These drawings are not necessarily drawn to scale. In order to better appreciate how the above-recited and other advantages and objects are obtained, a more particular description of the embodiments will be rendered, which are illustrated in the accompanying drawings. These drawings depict only typical embodiments and are not therefore to be considered limiting of its scope.

DESCRIPTION OF THE EMBODIMENTS

Figure 1:
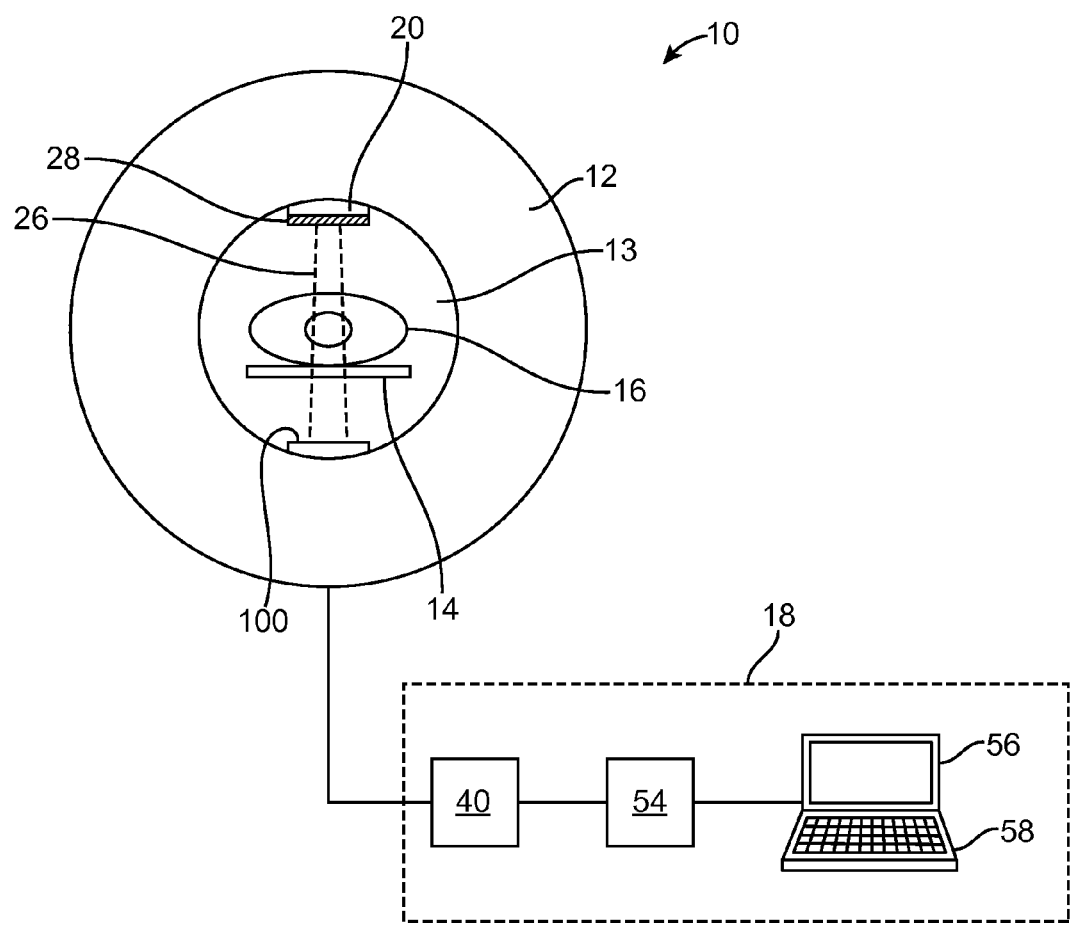
FIG. 1 illustrates a system for delivering radiation in accordance with a treatment plan determined in accordance with embodiments described herein.

Various embodiments are described hereinafter with reference to the figures. It should be noted that the figures are not drawn to scale and that elements of similar structures or functions are represented by like reference numerals throughout the figures. It should also be noted that the figures are only intended to facilitate the description of the embodiments. They are not intended as an exhaustive description of the invention or as a limitation on the scope of the invention. In addition, an illustrated embodiment needs not have all the aspects or advantages shown. An aspect or an advantage described in conjunction with a particular embodiment is not necessarily limited to that embodiment and can be practiced in any other embodiments even if not so illustrated.

FIG. 1 illustrates a radiation treatment system 10 for delivering radiation in accordance with a treatment plan that is determined using techniques described herein. The system 10 includes a gantry 12, a patient support 14 for supporting a patient, and a control system 18 for controlling an operation of the gantry 12. The system 10 also includes a radiation source 20 that projects a beam 26 of radiation towards a patient 16 while the patient 16 is supported on support 14, and a collimator system 28 for controlling a delivery of the radiation beam 26. The radiation source 20 can be configured to generate a cone beam, a fan beam, or other types of radiation beams in different embodiments.

In the illustrated embodiments, the radiation source 20 is a treatment radiation source for providing treatment energy. In other embodiments, in addition to being a treatment radiation source, the radiation source 20 can also be a diagnostic radiation source for providing diagnostic energy. In such cases, the system 10 will include an imager such as the imager 100, located at an operative position relative to the source 20 (e.g., under the support 14). In some embodiments, the treatment energy is generally those energies of 160 kilo-electron-volts (keV) or greater, and more typically 1 mega-electron-volts (MeV) or greater, and diagnostic energy is generally those energies below the high energy range, and more typically below 160 keV. In other embodiments, the treatment energy and the diagnostic energy can have other energy levels, and refer to energies that are used for treatment and diagnostic purposes, respectively. In some embodiments, the radiation source 20 is able to generate X-ray radiation at a plurality of photon energy levels within a range anywhere between approximately 10 keV and approximately 20 MeV. Radiation sources capable of generating X-ray radiation at different energy levels are described in U.S. patent application Ser. No. 10/033,327, entitled "RADIOTHERAPY APPARATUS EQUIPPED WITH AN ARTICULABLE GANTRY FOR POSITIONING AN IMAGING UNIT," filed on Nov. 2, 2001, and U.S. patent application Ser. No. 10/687,573, entitled "MULTI-ENERGY X-RAY SOURCE," filed on Oct. 15, 2003. In further embodiments, the radiation source 20 can be a diagnostic radiation source. In the illustrated embodiments, the radiation source 20 is coupled to the gantry 12. Alternatively, the radiation source 20 may be located within a bore.

In the illustrated embodiments, the control system 18 includes a processor 54, such as a computer processor, coupled to a control 40. The control system 18 may also include a monitor 56 for displaying data and an input device 58, such as a keyboard or a mouse, for inputting data. In the illustrated embodiments, the gantry 12 is rotatable about the patient 16, and during a treatment procedure, the gantry 12 rotates about the patient 16 (as in an arch-therapy). In other embodiments, the gantry 12 does not rotate about the patient 16 during a treatment procedure. In such case, the gantry 12 may be fixed, and the patient support 14 is rotatable. The operation of the radiation source 20, the collimator system 28, and the gantry 12 (if the gantry 12 is rotatable), are controlled by the control 40, which provides power and timing signals to the radiation source 20 and the collimator system 28, and controls a rotational speed and position of the gantry 12, based on signals received from the processor 54. Although the control 40 is shown as a separate component from the gantry 12 and the processor 54, in alternative embodiments, the control 40 can be a part of the gantry 12 or the processor 54.

It should be noted that the system 10 is not limited to the configuration described above, and that the system 10 may have other configurations in other embodiments. For example, in other embodiments, the system 10 may have a different shape. In other embodiments, the radiation source 20 of the system 10 may have different ranges of motions and/or degrees of freedom. For example, in other embodiments, the radiation source 20 may be rotatable about the patient 16 completely through a 360° range, or partially through a range that is less than 360°. Also, in other embodiments, the radiation source 20 is translatable relative to the patient 16. In further embodiments, the source 20 may be coupled to the gantry 12 via an arm, in which case, the source 20 is located outside the bore of the gantry 12.

Although the above embodiments have been described with reference to delivering treatment radiation that is in the form of x-rays, in other embodiments, the system and technique described herein may be used for other types of treatment energy. For examples, in other embodiments, in other embodiments, the radiation source 20 may be a proton source for delivering protons to treat a patient, an electron source for delivering electrons, or other types of particle source for delivering other types of particles for treating patient. Accordingly, embodiments of the treatment planning technique described herein may be used to determine treatment plan for other types of treatment, such as proton treatment, which may be considered to be a type of radiation treatment. Also, it should be noted that the term "collimator" is not limited to a device having leaves for blocking radiation, and may refer to a device having one or more jaws or jaw blocks. Thus, a position of a collimator may refer to position of leaves of a collimator, position of collimator jaws, or a global position of the collimator itself relative to some coordinate system (e.g., a position of the collimator relative to a gantry or relative to a radiation machine, etc.).

Figure 2:
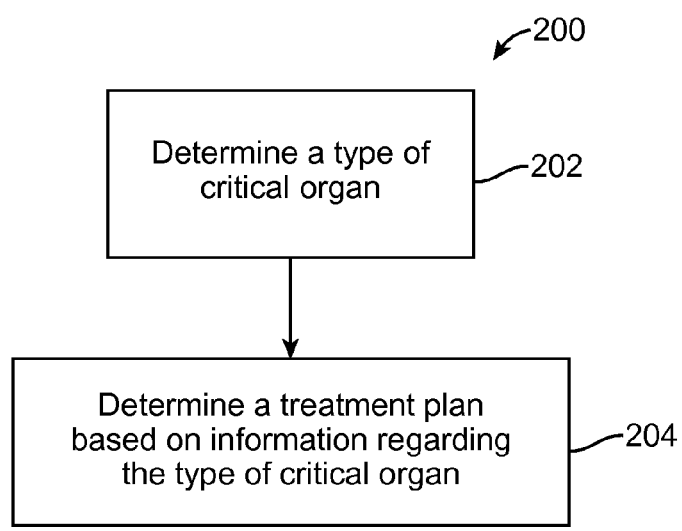
FIG. 2 illustrates a method for determining a treatment plan in accordance with some embodiments.

A method 200 for use to determine a treatment plan will now be described with reference to FIG. 2. The treatment plan may be used by the system 10 of FIG. 1 in some embodiments, but may also be used by other systems in other embodiments. First, a type of critical organ is determined (step 202). As used in this specification, the term "critical organ" refers to any tissue that is not a part of a target tissue (e.g., tumorous tissue that is desired to be irradiated). For example, a critical organ may refer to healthy tissue, which may or may not be directly next to the target tissue. Also, a critical organ may be a part of an organ or the entire organ itself. For example, in some cases, two critical organs may be parts of the same organ. In some embodiments, the act of determining the type of critical organ may be accomplished by a processor (such as processor 54 or another processor), which receives input from a user regarding the type of critical organ. For example, in some embodiments, the processor may receive input from a user indicating that a certain healthy tissue is a parallel critical organ, or a serial critical organ. In other embodiments, the act of determining the type of critical organ may be performed by the processor calling, loading, or retrieving a program or a function that includes information regarding a critical organ type.

As used in this specification, the term "parallel critical organ," or similar term(s), refers to an organ or a part of an organ, in which different regions perform the same function. Because same function is performed by different parts of the organ, different parts of the parallel organ do not depend on each other, and some parts may be damaged without significantly affecting the function of the remaining parts of the organ. An example of parallel critical organ is muscle, because if one region of the muscle is damaged, other parts of the muscle can still perform the work.

Also, as used in this specification, the term "serial critical organ," or similar term(s), refers to an organ or a part of an organ, in which one or more parts function in series. In serial critical organ, if one part is damaged, one link of the chain of function will be missing and the overall function of the organ does not work very well (or at all). An example of a serial organ is spinal cord, because if one part of the spinal cord is broken or damaged, then signals will not be able to pass through, and the organ is not very useful.

Figure 3:
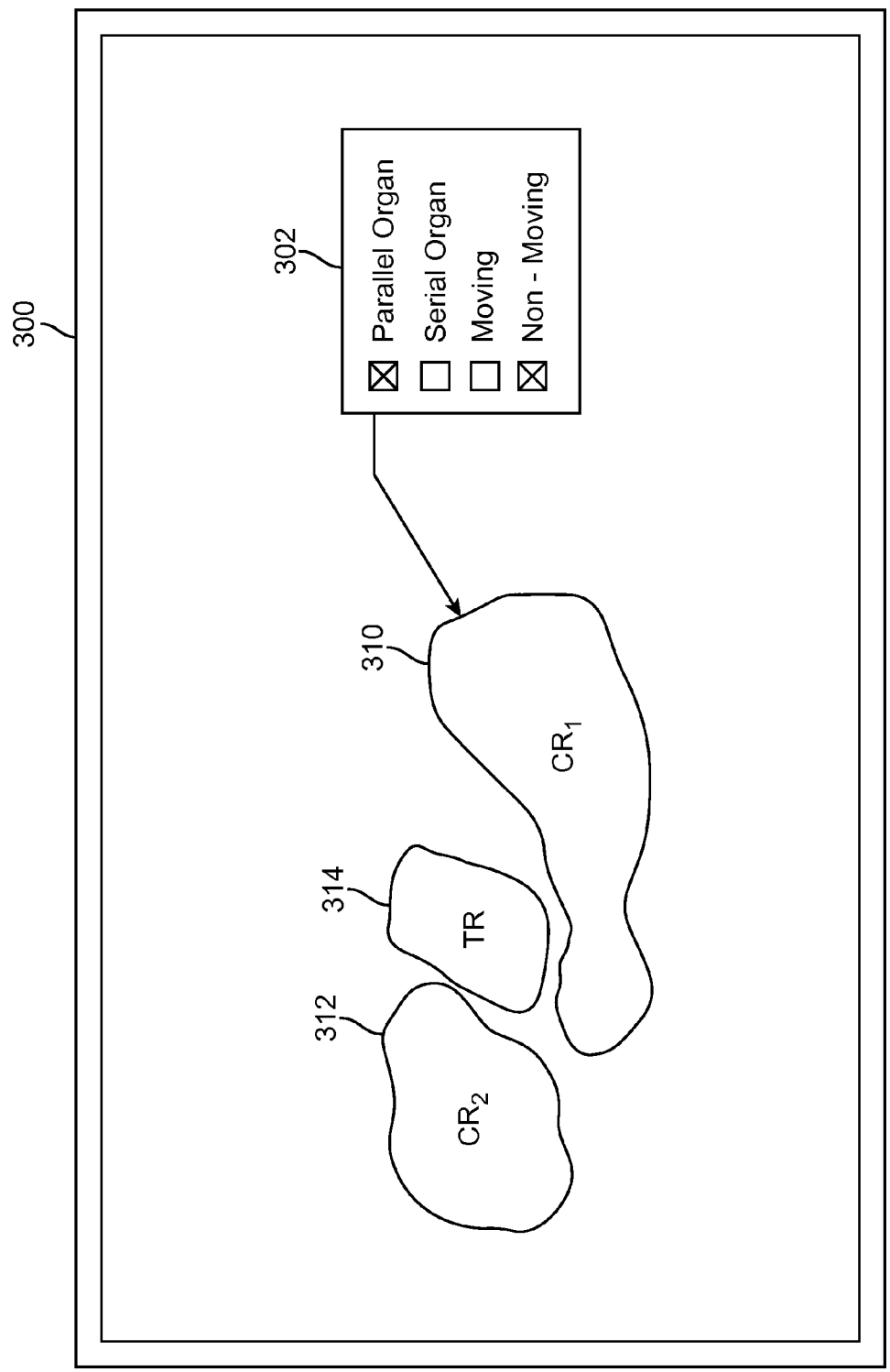
FIG. 3 illustrates a user interface displaying critical organs adjacent to a target region.

In the illustrated embodiments, the processor may provide a user interface that allows the user to select the type of critical organ for characterizing a certain healthy tissue. For example, the user interface may include a screen 300 displaying critical organs $CR_1$, $CR_2$ next to a target region TR (FIG. 3). The screen 300 may also display an input field 302 that identifies a plurality of types of critical organ, and the user may select one or more of the types to characterize the healthy tissue. In other embodiments, instead of, or in addition to, providing "parallel" type and "serial" type, the processor may also provide other types of critical organ for the user to select. For example, the processor may allow the user to indicate whether a healthy tissue is moving or non-moving. Other types of critical organ may also be provided by the processor in other embodiments.

In some embodiments, the processor may allow the user to characterize different healthy tissues into different types for a same treatment plan. For example, if there are two healthy tissues 310, 312 adjacent to a target tissue 314 that need to be considered in a treatment plan, the user may characterize the first healthy tissue 310 differently from the second healthy tissue 312 (FIG. 3). In the illustrated example, the first healthy tissue 310 may be characterized as a parallel organ, while the second healthy tissue 312 may be characterized as a serial organ. In another example, the first healthy tissue 300 may be characterized as a moving organ, while the second healthy tissue 302 may be characterized as a non-moving organ. In still another example, the first healthy tissue 300 may be characterized as a parallel organ that is moving, while the second healthy tissue 302 may be characterized as a parallel organ that is non-moving. Other combination of characterizing different healthy tissues may be used in other embodiments.

Figure 4:
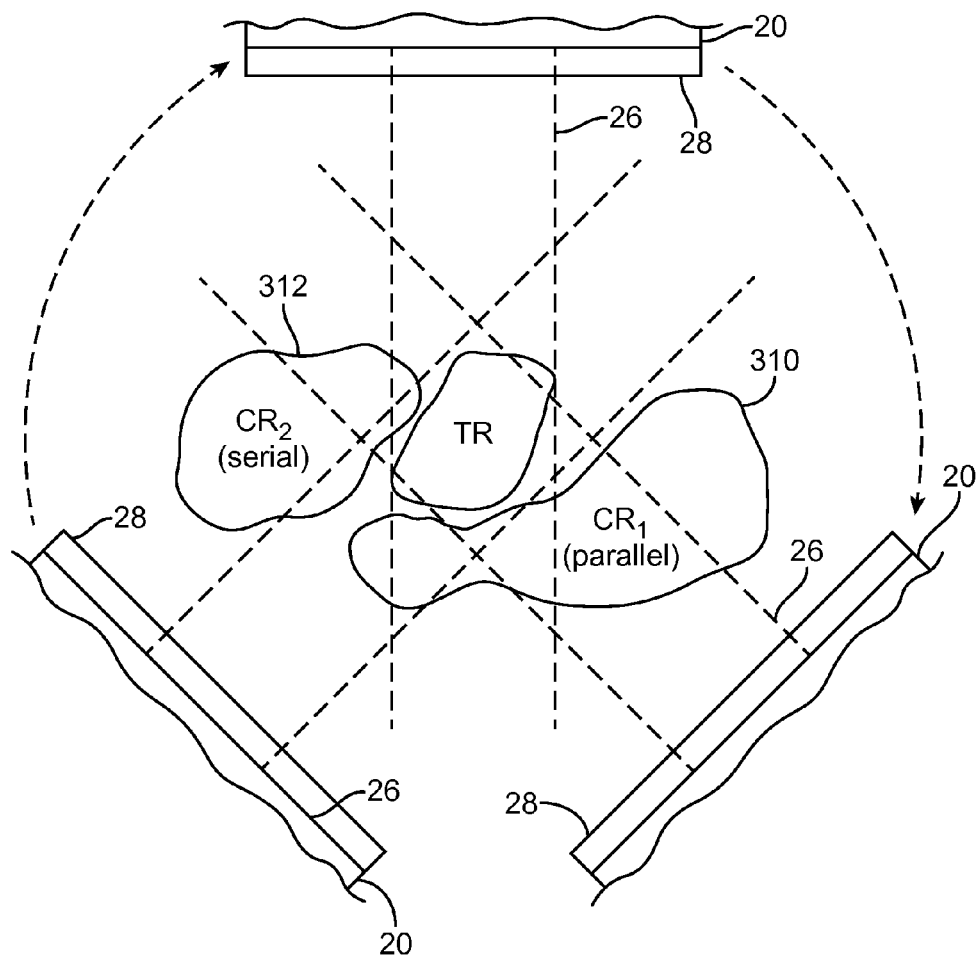
FIG. 4 illustrates a technique of accumulating dose and imposing constraint(s) based on a type of critical organ.

Referring back to FIG. 2, next, the processor determines a treatment plan based on the information regarding the type(s) of critical organ (step 204). The treatment plan will be described with reference to arc therapy in which the radiation source 20 rotates about a target region TR and delivers radiation 26 from a plurality of gantry angles (FIG. 4). However, it should be understood that the embodiments described herein are not limited to arc therapy, and that they are applicable to other types of treatment. In the illustrated example, there are two critical organs 310, 312 that are adjacent to the target region TR. In other examples, there may be only one critical organ, or more than two critical organs. Also, in other examples, the critical organ(s) and the target region may have configurations that are different from those illustrated in the example of FIG. 4. For example, in other embodiments, the critical organs 310, 312 may be parts of the same organ structure.

One objective of the treatment planning is to determine a set of fluences for respective gantry angles such that radiation dose accumulated at the target region TR is above a prescribed minimum dose, and that radiation dose accumulated at each of the critical organ(s) CR satisfies a certain dose criteria. In some embodiments, such objective may be represented by an objective function that is expressed as a function of different variables desired to be considered during the treatment planning. Example of parameters that may be included in the objective function include target fluence, a dose, a dose rate, a gantry position, a gantry speed, positions of leaves (i.e., collimator configuration), a beam energy, a beam-on condition, and a beam-off condition. Such parameters may be included in the objective function f, in which case, the optimization of the function f may be performed to determine these parameters. Objective functions for treatment planning and optimization techniques for objective functions are well known, and therefore, will not be described in further details.

In the illustrated embodiments, the type(s) of critical organ is taken into consideration during the treatment planning. In particular, based on the type(s) of a critical organ, the processor may be configured to impose a certain type of constraint, apply a certain dose accumulation technique, consider a deviation from planned dose or planned position in a certain way, and/or consider organ's movement using a certain technique. Each of these may be incorporated in the objective function, and is described below.

1. Different Types of Constraint for Different Types of Critical Organ:

In some embodiments, the processor is configured to impose different types of constraint for different types of critical organ. For parallel organ, the processor may be configured (programmed and/or built) to impose the constraint that the average dose or total dose (=average dose*volume of organ) for a critical organ be as low as possible. On the other hand, for serial organ, the processor may be configured to impose the constraint that the maximum dose for a critical organ be as low as possible. This is because for parallel organ, the distribution of dose may not be important. However, maximum dose for serial organ is important, because the part that is damaged the most will dictate the functionality of the organ. Thus, in the illustrated embodiments, when determining the treatment plan, optimization technique is performed on the objective function while imposing the conditions that average/total dose for each of the parallel critical organ(s) be below a prescribed average/total dose constraint, and that the maximum dose for each of the serial critical organ(s) be below a prescribed maximum dose constraint. Average (or total) dose constraint is considered to be a different type of constraint from the maximum dose constraint.

In some embodiments, although the same type of dose constraint is applied for critical organs that belong to the same type, different values for the same type of dose constraint may be applied for different critical organs that belong to the same type. For example, if there are two critical organs that are both parallel organ, then the same type of dose constraint, i.e., average/total dose constraint, may be applied for these two critical organs, but different constraint values for such constraint type may be applied for the two parallel critical organs. For example, the first parallel critical organ may have an average dose constraint of 50 Gy imposed thereon (e.g., the average dose on the first parallel critical organ cannot exceed 50 Gy), and the second parallel critical organ may have an average dose constraint of 60 Gy imposed thereon. Similarly, if there are two critical organs that are both serial organ, then the same type of dose constraint, i.e., maximum dose constraint, may be applied for these two serial critical organs, but different constraint values for such constraint type may be applied for the two serial critical organs. For example, the first serial critical organ may have a maximum dose constraint of 65 Gy imposed thereon (e.g., the maximum dose at any point/region in the first serial critical organ may not exceed 65 Gy), and the second serial critical organ may have a maximum dose constraint of 80 Gy imposed thereon.

Also, in some embodiments, the processor may use different constraints for different movement scenarios of a critical organ. For example, the constraints (e.g., dose constraints) may be used to evaluate a treatment plan in different movement scenarios. In other embodiments, the processor may use different constraints for different respective critical organs that have different movement behaviors. For example, in some cases, a first constraint (e.g., dose constraint) for a heart, and a second constraint for a lung may be used to evaluate a treatment plan. The first constraint may be of the same type as the second constraint, in which case, the constraint values for the first and second constraints may be different. Alternatively, the first constraint may be of a different type from that of the second constraint.

2. Different Dose Accumulation Techniques for Different Types of Critical Organ:

In some embodiments, the processor is configured to use different dose accumulation techniques for different types of critical organ. As fluence from different gantry angles are being applied incrementally at the target region TR, the accumulated dose at the target region TR will increases (FIG. 4). At the same time, the accumulated dose at the adjacent critical organs $CR_1$, $CR_2$ will also increase because some of the rays that traverse the target region TR also traverse part(s) of the critical organ(s) $CR_1$, $CR_2$. In the illustrated embodiments, for parallel organ, the processor is configured to accumulate dose and keep track of different accumulated doses for different parts of the parallel organ, and calculate an average dose from the set of accumulated doses for the parallel organ. Such may be performed, for example, for each gantry angle or for each control point. In some embodiments, the accumulated dose and/or the average accumulated dose may be represented as variable(s) in the objective function, which allows such parameter(s) to be considered when optimization is performed on the objective function to determine the treatment plan. The average dose constraint described previously is imposed on the parallel critical organ such that the average accumulated dose cannot exceed the average dose constraint.

Similarly, in the illustrated embodiments, for serial critical organ, the processor is configured to accumulate dose and keep track of different accumulated doses for different parts of the serial critical organ, and determine a maximum accumulated dose from the set of accumulated doses for the serial organ. Such may be performed, for example, for each gantry angle or for each control point. In some embodiments, the accumulated dose and/or the maximum accumulated dose may be represented as variable(s) in the objective function, which allows such parameter(s) to be considered when optimization is performed on the objective function to determine the treatment plan. The maximum accumulated dose constraint described previously is imposed on the serial critical organ such that the maximum accumulated dose cannot exceed the maximum accumulated dose constraint.

In some cases, the critical organ(s) may be moving, such as due to breathing. One technique for considering breathing motion when modeling dose accumulation in the method is to model the motion as two (or more) different states: e.g., inhale state and exhale state. In some treatment, half of the beam delivery may occur when the lungs fully exhale (in the exhale state), and the other half of the beam delivery may occur when the lungs fully inhale (in the inhale state). One way to model dose accumulation in this situation is to assume that half of the dose is delivered in the exhale state, and the other half of the dose is delivered in the inhale state, and sum the doses. However, the actual treatment may be different. For example, 10% of the radiation delivery time might be spent in the inhale state, and 90% of the radiation delivery time might be spent in the exhale state, or vice versa. Often, one does not know in advance what is the actual movement pattern (and therefore, the actual amount of radiation delivery time spent in the inhale and exhale states) during treatment. The worst case scenario might be different for different organs. For example, radiation delivered during the exhale state may be worse for spinal cord and radiation delivered during the inhale state might be worst for heart. In this case, a movement pattern with 90% of the radiation time in the exhale state may be bad for spinal cord and the movement pattern with 90% of the time spent in the inhale state may be bad for heart. For serial organs, the maximum dose should not exceed in the worst case scenario, and the worst case scenario occurs with different movement pattern for different organs. In the example, the processor may be configured to evaluate the part of the objective function for the spinal cord using a movement pattern that is bad for the spinal cord (because it might occur during treatment), and evaluate the part of the objective function for the heart using a movement pattern that is bad for heart (because it might also happen during treatment). The movement pattern that is bad for the spinal cord may be different from the movement pattern that is bad for the heart, but both are considered during the treatment planning in the illustrated embodiments. A treatment optimized in this manner would be safe for all critical organs no matter which of the evaluated movement patterns actually occur during the treatment.

For moving organ(s), there are multiple possible movement trajectories that may occur. Thus, in some embodiments, for each of the moving organ(s), the processor is configured to consider different movement trajectories, and evaluate the worst case scenario for each organ (e.g., by determining the movement trajectory that results in the worst case for the organ). In some embodiments, the processor is configured to evaluate different movement trajectories for each critical organ. For example, different movement trajectories may be represented using weights that correspond to different movement states. In one implementation, each weight may represent a percentage of irradiation time spent on the corresponding movement state (e.g., inhale/exhale state). In such cases, the processor is configured to consider different movement trajectories by evaluating the dose effect resulted from different combination of weights (or percentages of irradiation time spent on each of the movement phases). The different movement trajectories may be evaluated using (e.g., by evaluating) the organ-type specific constraint. For each organ, the processor is configured to include the trajectory that is most significant (e.g., one that produces the worst case scenario) in the objective function. In some cases, for moving parallel organ(s), simplified accumulation methods may be used to speed up the evaluation of different trajectories.

In some embodiments, different dose accumulation methods may be used for organs that have different movement behaviors. For example, in some cases, one organ (e.g., critical organ) may move differently from another organ, in which cases, different dose accumulation techniques may be used for the respective organs. In other cases, one organ may move, and another organ may be relatively stationary (which may be considered a special case of "movement" scenario). In such cases, different dose accumulation techniques may be used for the moving organ and the stationary organ.

3. Consideration of Uncertainty in Dose Distribution Based on Type of Critical Organ:

The patient may move during treatment, due to, for examples, breathing or cardiac movement. As a result, organs may move while radiation is being delivered, and therefore there is uncertainty in the dose distribution. Stationary objects are not affected by correlation effects with dynamic treatment. Therefore one can assume that they receive a dose that is closer to planned dose and simple average modeling. In some embodiments, the actual position of a stationary organ may be allowed to have more deviation from the planned position. Alternatively or additionally, more dynamics in treatment may be allowed for regions that involve stationary object(s) (for example, more complex fluence may be allowed during treatment planning in regions where an object is stationary compared to an object that is mobile). Also, in some embodiments, a stationary serial organ could have a maximum dose that is closer to the maximum dose constraint than a serial organ that is mobile. On the other hand, mobile objects, especially serial organs, need to have some extra room to allow some deviations from planned situation. For such purpose, a smaller maximum dose constraint may be used for serial organs. Such technique may decrease the probability that a maximum dose for a part of the serial organ will exceed a prescribed maximum dose (maximum dose constraint).

In some embodiments, different movement patterns for different types of critical organs may be addressed by prescribing different respective weights, or different respective sets of weights. In particular, the relevant set of weights may be different for different organ types. For example, one set of weights might be very harmful for spinal cord, but another set of weights might be very harmful for heart. Both of these possible sets of weights (which are associated with different movement patterns that might occur during treatment) should be considered during optimization, because one does not want to loose either the heart or the spinal cord, no matter which one happens to occur.

Also, because there is some uncertainty associated with patient movement, one does not know in advance how much time will be spent in each physiological phase during treatment. Thus, in some embodiments, each movement phase may have its own weight or set of weights. In the illustrated embodiments, the processor is configured to calculate dose for the selected weight(s) or the selected set of weights (either of which is critical organ type specific), and then calculate dose volume histograms (DVHs) from that dose. DVH is a function that describes what fraction of volume has received dose that is smaller than some value. For example, DVH(x)=v, where x is dose level and v is the fraction that receives less than x dose. In one implementation, the dose is first calculated by the processor for each movement phase. Then some weight is chosen (either by input from a user, or automatically by the processor based on pre-programming) for each phase. The processor then calculates a combined dose using the selected weights (which are critical organ type specific) for each movement phase, and calculates the DVH from that dose distribution. In another implementation, the processor is configured to calculate DVHs for each phase and then calculate weighted average of the DVHs, wherein the weight(s) used is critical organ type specific. Different sets of weights produce different DVHs. The relevant set of weights for one organ may be different from that for another organ. Since parallel organs depend more on the most likely case, while serial organs must avoid worst case scenario, it may be useful to consider average or likely set of weights for parallel organs and find the worst set of weights for serial organs. Average set for weights in above example could be, for example, 50% of irradiation time in lung empty state, and 50% of irradiation time in lung full state. Alternatively, it could be average time spent in each state if the motion was recorded for a long period of time. The worst set of weight is one that would produce the worst objective function value component for the specific organ.

4. Movement Consideration:

In some embodiments, the processor is configured to handle mobile and stationary structures in different ways. In some embodiments, when dealing with movement of a parallel critical organ, the processor may assume that the parallel critical organ is one large organ that covers the whole movement region. Such technique is advantageous in that it allows computation of dose for a moving organ to be simplified, while allowing the average/total dose for the organ to be determined accurately. On the other hand, for serial critical organ, the processor may model the movement of the serial critical organ as accurately as possible, while allowing small deviations of the actual position from the planned position.

In some cases, several different outcomes for the same treatment plan are possible, because the actual organ movement during treatment is not known in advance. Therefore different assumed movements produce different dose distributions. These dose distributions deviate from the prescribed dose levels in different way, and the deviations form a distribution of deviations. In some embodiments, organ specific objective functions (that consider distribution of deviations) are evaluated first, and the total objective function is calculated from individual organ specific objective functions. Such technique allows the most important deviation, which is organ type specific, to be considered for each organ. For examples, for parallel organs, such deviation may correlate with the average of possible doses, and for serial organs, such deviation may correlate with the maximum dose of possible movement instances.

In some embodiments, when performing the method 200, multiple phases of a physiological cycle may contribute in the objective function for one organ. In such cases, information regarding a planned dose is first determined considering all phases for one organ (such as average dose or maximum dose of each phase—depending on the types of critical organ). The total objective function is then formed from the structure contributions (e.g., contributions from different critical organs). Such technique is advantageous over the technique in which the objective function is calculated first for each phase separately, and then a worst or average is optimized. This is because the worst case for some organ may be a combination of many phases, and for another organ, it may be a different combination of phases. This would not be observed in existing models. This is because in existing models, phase specific objective function is calculated first, and the total objective function is determined from the phase specific objective functions.

As illustrated in the above embodiments, by considering the type of critical organ during treatment planning, the biological characteristic (e.g., function, behavior, etc.) of the critical organ and its effect on the treatment are taken into consideration during treatment planning. This is advantageous in that it allows a more accurate treatment plan to be determined and a more desirable treatment result to be obtained. Also, by applying different types of constraint(s) and different dose accumulation techniques for different types of critical organ, specific clinical objectives (e.g., minimizing average/total dose, minimizing maximum dose, etc.) that are relevant for the specific organ types can be achieved.

After the treatment plan has been determined, the treatment plan may be stored in a medium for later use. For example, the treatment plan may be later loaded into a computer system for evaluating the treatment plan by carrying out the treatment plan using a phantom. In another example, the treatment plan may be later loaded into a computer system, which is configured to carry out the treatment plan by performing a treatment procedure on the patient. When carrying out the treatment plan (on the phantom or the patient), the techniques for considering the different types of critical organ discussed previously may be applied.

Figure 5:
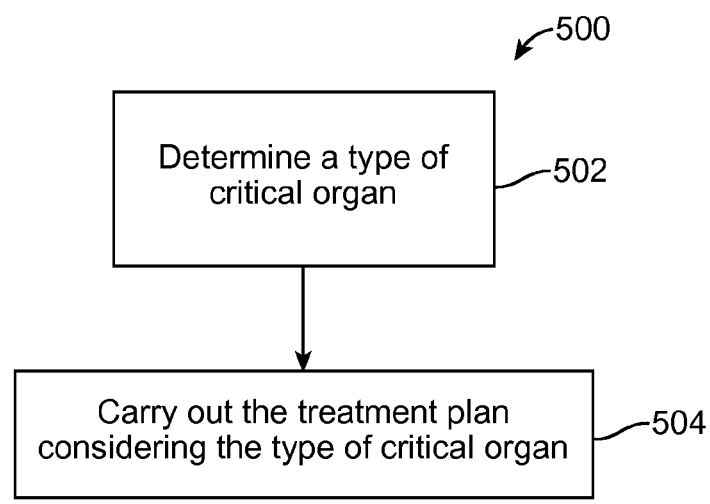
FIG. 5 illustrates a method for executing a treatment plan in accordance with some embodiments.

FIG. 5 illustrates a method 500 for executing a treatment plan that considers the type of critical organ(s). First, the processor 54 (or another processor) determines a type of critical organ (step 502). In some embodiments, this may be accomplished by the processor 54 receiving the treatment plan that identifies the critical organ and the type for the critical organ. Sometimes, the treatment plan may involve a plurality of critical organs. In such cases, the processor is configured to determine the type of critical organ for each of the plurality of critical organs. In other embodiments, the act of determining the type of critical organ may be accomplished by the processor calling, loading, or retrieving a program or a function that includes information regarding a critical organ type.

Next, the processor then carries out the treatment plan considering the type(s) of critical organ. In some embodiments, during an execution of the treatment plan to treat the patient, the processor may be configured to receive information regarding an actual dose delivered to each of the critical organ(s). Following the example of FIG. 4, during the actual treatment session, first dose information (e.g., dose from different gantry angles) for critical organ 310, and second dose information (e.g., dose from different gantry angles) for critical organ 312 may be received by the processor. The processor is configured to accumulate the actual dose for each of the critical organs 310, 312 based on the types of the critical organs 310, 312.

In the illustrated example, because the critical organ 310 is a parallel organ, the processor is configured to determine and keep track of the average or total (=average dose*volume of organ) dose for the critical organ 310 as the treatment is being carried out. On the other hand, because the critical organ 312 is a serial organ, the processor is configured to determine and keep track of the maximum dose for the critical organ 312 as the treatment is being carried out. In some cases, the average or total dose for the critical organ 310, and the maximum dose for the critical organ 312, may be determined for each gantry angle (or for each control point) of the radiation source 20. The processor keeps track of the average or total dose for the organ 310, and if it exceeds the constraint value (for the constraint type for the parallel organ) imposed for the parallel organ 310, then the processor may be configured to generate a signal to stop the delivery of radiation and/or to inform the physician/operator that the dose criteria for the parallel organ 310 has been exceeded. Similarly, the processor keeps track of the maximum dose for the organ 312, and if it exceeds the constraint value (for the constraint type for the serial organ) imposed for the serial organ 312, then the processor may be configured to generate a signal to stop the delivery of radiation and/or to inform the physician/operator that the dose criteria for the serial organ 312 has been exceeded.

In the above embodiments, the methods 200, 500 have been described with reference to the radiation source 20 rotating about the target, as in an arc therapy. However, it should be understood that the methods 200, 500 are not limited to the example illustrated, and that the methods 300, 500 may be used to determine and execute treatment plan for systems with different configurations. For example, in other embodiments, the radiation source 20 may be configured to translate, instead of rotating, relative to the target. In other embodiments, the patient support 14 may be configured to position the patient in different degrees of freedom, thereby providing different trajectories for delivering radiation towards the target region.

Also, in further embodiments, the methods 200, 500 may be used to respectively determine and execute a treatment plan for intensity modulated radiation therapy (IMRT). In IMRT, the collimator is operated to control the leaves such that different parts of the same target region receive different amount of doses. In such cases, information regarding the different desired dose for different parts of the target region, and information regarding the constraints for the operation of the collimator (e.g., orientation of collimator, leaves' speed, etc.) are incorporated into the objective function during treatment planning.

In some embodiments, a treatment plan for IMRT that considers organ movement may be determined by optimizing a set of fluences (one per IMRT field), and it is assumed that this set of fluences is delivered to all phases of a physiological cycle. Then DVHs of different phases are calculated and the information of DVHs is combined to obtain a single objective function value. Machine limitations may limit the shapes of fluences that can be delivered in a given period (e.g., very short, such as within seconds) of time. In some cases, the optimized fluence is actually delivered as a set of fluence components (also referred to as fluences) that can be delivered by the machine, and the sum of the fluence components is the planned/optimized fluence. Because the fluence is actually delivered in components, the delivery of a planned fluence takes some time. During this time the patient may move. For example the delivery of a fluence may be started when patient's lung is in an exhale state, and the delivery of the fluence may end when the patient's lung is in an inhale state. The sum of the fluence components is the same as that planned, but some of the components were delivered during the exhale state, and some during the inhale state. Therefore the actual fluence delivered in the exhale state could be different from that delivered in the inhale state, wherein both of which may be different from the planned fluence. In some embodiments, the processor is configured to perform an approximation by assuming that the same planned fluence is delivered in all phases. The inaccuracy produced by this assumption is decreased by using the embodiments of the technique(s) described herein, because the worst case is considered by the processor.

In some embodiments, the processor is configured to determine a four dimensional IMRT treatment plan. In such cases, an objective function that considers the type(s) of critical organ(s) is defined. It combines a chosen set of objectives (e.g., minimizing average/total dose for parallel critical organ such that it is below a prescribed constraint, minimizing maximum dose for serial critical organ such that it is below a prescribed constraint, delivering as much of the prescribed dose to target region as possible, etc.), and converts them to a single scalar value. A four dimension (the 4th dimension being time) IMRT fluence optimization is then performed by performing the following steps: (1) Calculate dose from the fluences for each phase, (2) Calculate objective function derivatives and project them back to fluence space, (3) Modify the fluence space based on the objective function derivatives, (4) iterate steps 1-3 until a solution converges, and (5) convert the fluences that correspond to the converged solution to leaf sequence using a leaf sequencing algorithm (which is known in the art). IMRT and optimization methods for IMRT are known in the art, and therefore will not be described in further detail. In some embodiments, with respect to steps (2) and (3) above, the derivatives of the objective function with respect to fluence are back-projected to a fluence map and are used to manipulate the fluence. For example, if the objective function would decrease in correlation with a decrease of dose for a control point, then the fluence in the corresponding (projected) position would be decreased to decrease the dose for that control point.

Computer System Architecture

Figure 6:
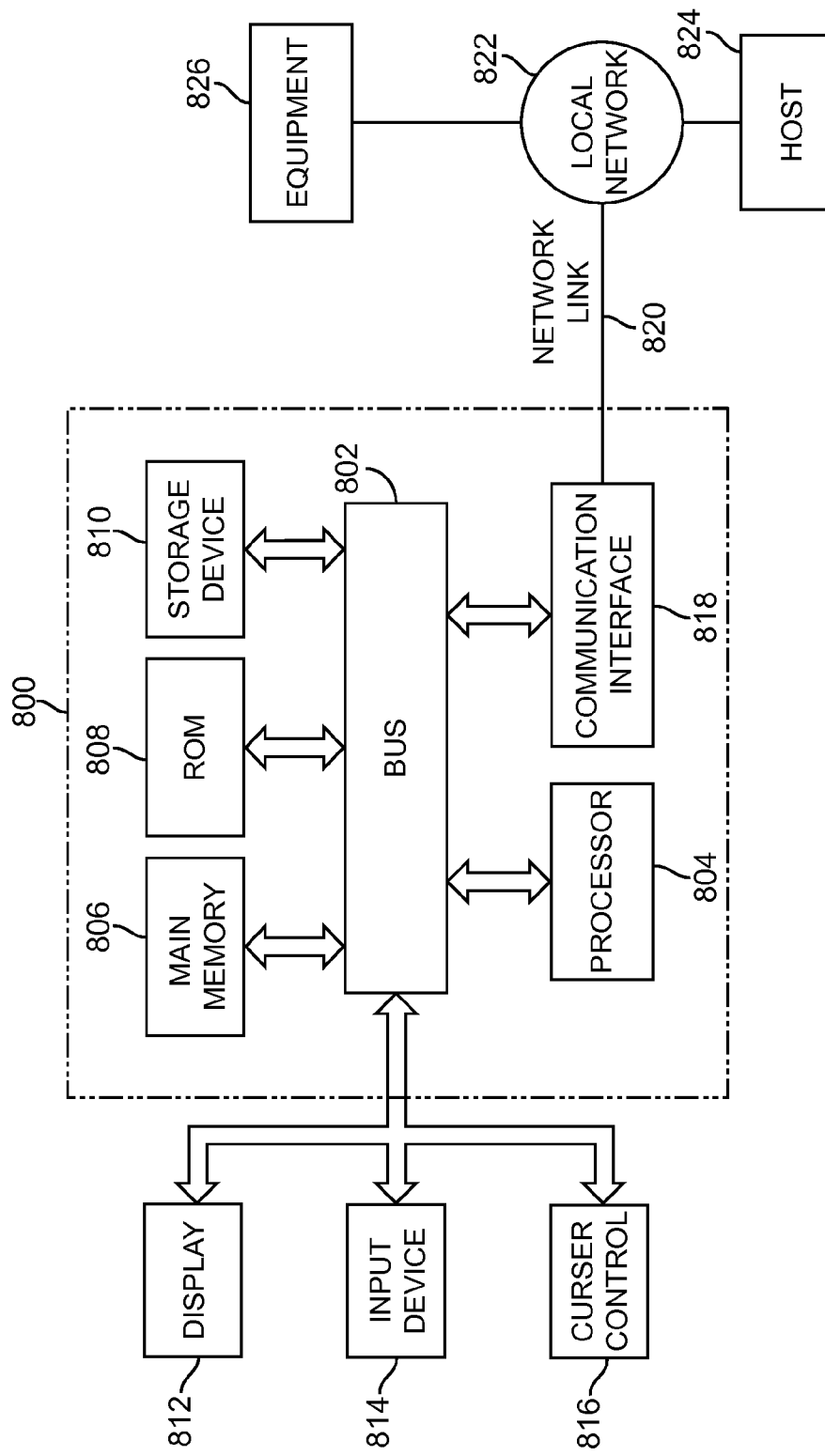
FIG. 6 is a block diagram of a computer system architecture, with which embodiments described herein may be implemented.

FIG. 6 is a block diagram that illustrates an embodiment of a computer system 1200 upon which an embodiment of the invention may be implemented. Computer system 800 includes a bus 802 or other communication mechanism for communicating information, and a processor 804 coupled with the bus 802 for processing information. The processor 804 may be an example of the processor 54 of FIG. 1, or another processor that is used to perform various functions described herein. In some cases, the computer system 800 may be used to implement the processor 54. The computer system 800 also includes a main memory 806, such as a random access memory (RAM) or other dynamic storage device, coupled to the bus 802 for storing information and instructions to be executed by the processor 804. The main memory 806 also may be used for storing temporary variables or other intermediate information during execution of instructions to be executed by the processor 804. The computer system 800 further includes a read only memory (ROM) 808 or other static storage device coupled to the bus 802 for storing static information and instructions for the processor 804. A data storage device 810, such as a magnetic disk or optical disk, is provided and coupled to the bus 802 for storing information and instructions.

The computer system 800 may be coupled via the bus 802 to a display 812, such as a cathode ray tube (CRT) or a flat panel, for displaying information to a user. An input device 814, including alphanumeric and other keys, is coupled to the bus 802 for communicating information and command selections to processor 804. Another type of user input device is cursor control 816, such as a mouse, a trackball, or cursor direction keys for communicating direction information and command selections to processor 804 and for controlling cursor movement on display 812. This input device typically has two degrees of freedom in two axes, a first axis (e.g., x) and a second axis (e.g., y), that allows the device to specify positions in a plane.

The computer system 800 may be used for performing various functions (e.g., calculation) in accordance with the embodiments described herein. According to one embodiment, such use is provided by computer system 800 in response to processor 804 executing one or more sequences of one or more instructions contained in the main memory 806. Such instructions may be read into the main memory 806 from another computer-readable medium, such as storage device 810. Execution of the sequences of instructions contained in the main memory 806 causes the processor 804 to perform the process steps described herein. One or more processors in a multi-processing arrangement may also be employed to execute the sequences of instructions contained in the main memory 806. In alternative embodiments, hard-wired circuitry may be used in place of or in combination with software instructions to implement the invention. Thus, embodiments of the invention are not limited to any specific combination of hardware circuitry and software.

The term "computer-readable medium" as used herein refers to any medium that participates in providing instructions to the processor 804 for execution. Such a medium may take many forms, including but not limited to, non-volatile media, volatile media, and transmission media. Non-volatile media includes, for example, optical or magnetic disks, such as the storage device 810. Volatile media includes dynamic memory, such as the main memory 806. Transmission media includes coaxial cables, copper wire and fiber optics, including the wires that comprise the bus 802. Transmission media can also take the form of acoustic or light waves, such as those generated during radio wave and infrared data communications.

Common forms of computer-readable media include, for example, a floppy disk, a flexible disk, hard disk, magnetic tape, or any other magnetic medium, a CD-ROM, any other optical medium, punch cards, paper tape, any other physical medium with patterns of holes, a RAM, a PROM, and EPROM, a FLASH-EPROM, any other memory chip or cartridge, a carrier wave as described hereinafter, or any other medium from which a computer can read.

Various forms of computer-readable media may be involved in carrying one or more sequences of one or more instructions to the processor 804 for execution. For example, the instructions may initially be carried on a magnetic disk of a remote computer. The remote computer can load the instructions into its dynamic memory and send the instructions over a telephone line using a modem. A modem local to the computer system 800 can receive the data on the telephone line and use an infrared transmitter to convert the data to an infrared signal. An infrared detector coupled to the bus 802 can receive the data carried in the infrared signal and place the data on the bus 802. The bus 802 carries the data to the main memory 806, from which the processor 804 retrieves and executes the instructions. The instructions received by the main memory 806 may optionally be stored on the storage device 810 either before or after execution by the processor 804.

The computer system 800 also includes a communication interface 818 coupled to the bus 802. The communication interface 818 provides a two-way data communication coupling to a network link 820 that is connected to a local network 822. For example, the communication interface 818 may be an integrated services digital network (ISDN) card or a modem to provide a data communication connection to a corresponding type of telephone line. As another example, the communication interface 818 may be a local area network (LAN) card to provide a data communication connection to a compatible LAN. Wireless links may also be implemented. In any such implementation, the communication interface 818 sends and receives electrical, electromagnetic or optical signals that carry data streams representing various types of information.

The network link 820 typically provides data communication through one or more networks to other devices. For example, the network link 820 may provide a connection through local network 822 to a host computer 824 or to equipment 826 such as a radiation beam source or a switch operatively coupled to a radiation beam source. The data streams transported over the network link 820 can comprise electrical, electromagnetic or optical signals. The signals through the various networks and the signals on the network link 820 and through the communication interface 818, which carry data to and from the computer system 800, are exemplary forms of carrier waves transporting the information. The computer system 800 can send messages and receive data, including program code, through the network(s), the network link 820, and the communication interface 818.

Although particular embodiments have been shown and described, it will be understood that they are not intended to limit the present inventions, and it will be obvious to those skilled in the art that various changes and modifications may be made without departing from the spirit and scope of the present inventions. The specification and drawings are, accordingly, to be regarded in an illustrative rather than restrictive sense. The present inventions are intended to cover alternatives, modifications, and equivalents, which may be included within the spirit and scope of the present inventions as defined by the claims.

What is claimed:

1. A method for use in a treatment planning process or in a treatment process, comprising:
   determining a type of critical organ for healthy tissue; and
   determining a dose for the healthy tissue based on the type of critical organ;
   wherein the dose is an average accumulated dose if the type of critical organ is parallel, and the dose is a maximum accumulated dose if the type of critical organ is serial.

2. The method of claim 1, further comprising providing a plurality of types of critical organ for a user to select, and the act of determining the type of critical organ comprises receiving an input from the user representing a selection of one of the plurality of types of critical organ.

3. The method of claim 1, wherein the type of critical organ is parallel organ.

4. The method of claim 1, wherein the type of critical organ is serial organ.

5. The method of claim 1, wherein the dose is a variable, and the method further comprises:
   determining an objective function using information regarding the dose; and
   determining a treatment plan based on the objective function.

6. The method of claim 1, further comprising determining a treatment plan using information regarding the dose.

7. The method of claim 6, wherein the act of determining the treatment plan is performed during a treatment session.

8. The method of claim 1, wherein the act of determining the dose comprises accumulating actual dose delivered to a patient in a treatment session.

9. The method of claim 1, further comprising imposing a constraint based on the type of critical organ.

10. The method of claim 9, wherein the constraint comprises a prescribed average or total dose when the type of critical organ is parallel.

11. The method of claim 9, wherein the constraint comprises a prescribed maximum dose when the type of critical organ is serial.

12. The method of claim 1, further comprising evaluating an objective function for multiple movement trajectories of the healthy tissue, wherein the trajectories are organ-type specific.

13. The method of claim 12, further comprising determining a treatment plan using the objective function.

14. A system for use in a treatment planning process or in a treatment process, comprising a processor configured for:
    determining a type of critical organ for healthy tissue; and
    determining a dose for the healthy tissue based on the type of critical organ;
    wherein the processor is configured to determine an average accumulated dose as the dose if the type of critical organ is parallel, and determine a maximum accumulated dose as the dose if the type of critical organ is serial.

15. The system of claim 14, wherein the processor is further configured for determining a treatment plan using information regarding the dose.

16. The system of claim 14, wherein the dose is derived from an actual dose delivered to a patient in a treatment session.

17. The system of claim 14, wherein the type of critical organ is parallel, and the dose comprises the average accumulated dose.

18. The system of claim 14, wherein the type of critical organ is serial, and the dose comprises the maximum accumulated dose.

19. The system of claim 14, wherein the processor is further configured to evaluate an objective function for multiple movement trajectories of the healthy tissue, wherein the trajectories are organ-type specific.

20. The system of claim 19, wherein the processor is further configured to determine a treatment plan using the objective function.

21. A method for use in a treatment planning process or in a treatment process, comprising:
    determining a type of critical organ for healthy tissue; and
    determining a constraint for the healthy tissue based on different movement trajectories and the type of critical organ;
    wherein if the determined type is parallel, then the constraint comprises an average dose constraint, and if the determined type is serial, then the constraint comprises a maximum dose constraint.

22. The method of claim 21, further comprising providing a plurality of types of critical organ for a user to select, and the act of determining the type of critical organ comprises receiving an input from the user representing a selection of one of the plurality of types of critical organ.

23. The method of claim 21, wherein the type of critical organ is parallel organ.

24. The method of claim 21, wherein the type of critical organ is serial organ.

25. The method of claim 21, further comprising:
    applying the constraint for an objective function; and
    determining a treatment plan based on the objective function.

26. The method of claim 21, further comprising:
    obtaining dose information resulted from a delivery of radiation; and
    determining a treatment plan based on the dose information and the constraint.

27. The method of claim 21, further comprising:
    obtaining dose information resulted from a delivery of radiation; and
    performing a treatment procedure based on the dose information and the constraint.

28. The method of claim 21, wherein the constraint comprises a prescribed maximum dose for the critical organ, and the method further comprises minimizing a maximum dose for the critical organ so that the maximum dose is less than the prescribed maximum dose.

29. The method of claim 21, wherein the constraint comprises a prescribed average dose for the first critical organ, and the method further comprises minimizing an average dose for the critical organ so that the average dose is less than the prescribed average dose.

30. The method of claim 21, further comprising evaluating an objective function for multiple movement trajectories of the healthy tissue, wherein the trajectories are organ-type specific.

31. The method of claim 30, further comprising determining a treatment plan using the objective function.

32. A system for use in a treatment planning process or in a treatment process, comprising:
    a processor configured for receiving information regarding a type of critical organ for healthy tissue;
    wherein the processor is also configured for determining a constraint for the healthy tissue by based on different movement trajectories and the type of critical organ; and wherein the processor is configured to use an average dose constraint as the constrain if the type of critical organ is parallel, and a maximum dose constraint as the constraint if the type of critical organ is serial.

33. The system of claim 32, wherein the type of critical organ is parallel, and the constraint comprises the average dose.

34. The system of claim 32, wherein the type of critical organ is serial, and the constraint comprises the maximum dose.

35. The system of claim 32, wherein the processor is further configured to evaluate an objective function for multiple movement trajectories of the healthy tissue, wherein the trajectories are organ-type specific.

36. The system of claim 35, wherein the processor is further configured to determine a treatment plan using the objective function.

37. The method of claim 1, wherein the average accumulated dose is determined by obtaining different accumulated dose values for different parts of the healthy tissue, and calculating an average value of the accumulated dose values.

38. The method of claim 1, wherein the maximum accumulated dose is determined by obtaining different accumulated dose values for different parts of the healthy tissue, and selecting a maximum one of the accumulated dose values.

39. The method of claim 1, wherein the type of critical organ is determined as parallel when a function of a first part of the critical organ is independent of a function of a second part of the critical organ.

40. The method of claim 1, wherein the type of critical organ is determined as serial when a function of a first part of the critical organ is dependent on a function of a second part of the critical organ.

41. The system of claim 14, wherein the processor is configured to determine the average accumulated dose by obtaining different accumulated dose values for different parts of the healthy tissue, and calculating an average value of the accumulated dose values.

42. The system of claim 14, wherein the processor is configured to determine the maximum accumulated dose by obtaining different accumulated dose values for different parts of the healthy tissue, and selecting a maximum one of the accumulated dose values.

43. The system of claim 14, wherein the type of critical organ is parallel when a function of a first part of the critical organ is independent of a function of a second part of the critical organ.

44. The system of claim 14, wherein the type of critical organ is serial when a function of a first part of the critical organ is dependent on a function of a second part of the critical organ.

45. The method of claim 21, wherein the type of critical organ is determined as parallel when a function of a first part of the critical organ is independent of a function of a second part of the critical organ.

46. The method of claim 21, wherein the type of critical organ is determined as serial when a function of a first part of the critical organ is dependent on a function of a second part of the critical organ.

47. The system of claim 32, wherein the type of critical organ is parallel when a function of a first part of the critical organ is independent of a function of a second part of the critical organ.

48. The system of claim 32, wherein the type of critical organ is serial when a function of a first part of the critical organ is dependent on a function of a second part of the critical organ.

* * * * *